(12) United States Patent
McCulloch et al.

(10) Patent No.: US 9,030,495 B2
(45) Date of Patent: May 12, 2015

(54) AUGMENTED REALITY HELP

(71) Applicants: Daniel McCulloch, Kirkland, WA (US); Kudo Tsunoda, Bellevue, WA (US); Abby Lin Lee, Seattle, WA (US); Ryan Hastings, Seattle, WA (US); Jason Scott, Kirkland, WA (US)

(72) Inventors: Daniel McCulloch, Kirkland, WA (US); Kudo Tsunoda, Bellevue, WA (US); Abby Lin Lee, Seattle, WA (US); Ryan Hastings, Seattle, WA (US); Jason Scott, Kirkland, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 230 days.

(21) Appl. No.: 13/683,732

(22) Filed: Nov. 21, 2012

(65) Prior Publication Data

US 2014/0139551 A1  May 22, 2014

(51) Int. Cl.
*G09G 5/00* (2006.01)
*G09G 5/377* (2006.01)
*G02B 27/01* (2006.01)
G06F 9/44 (2006.01)
G06F 19/00 (2011.01)
G06F 19/10 (2011.01)

(52) U.S. Cl.
CPC ............. *G09G 5/377* (2013.01); *G06F 9/4446* (2013.01); *G06F 19/3406* (2013.01); *G06F 19/10* (2013.01); *G02B 27/017* (2013.01)

(58) Field of Classification Search
CPC .............. G06T 19/006; G06F 19/3406; G06F 19/3418; G06F 9/4446; G06F 17/30032; G06F 19/10; G06F 19/30

USPC ............ 345/633, 636; 715/705–715; 382/181
See application file for complete search history.

(56) References Cited

U.S. PATENT DOCUMENTS

| 5,583,795 | A | 12/1996 | Smyth |
| 7,330,197 | B2 | 2/2008 | Kobayashi et al. |
| 7,804,507 | B2 | 9/2010 | Yang et al. |
| 8,199,974 | B1 * | 6/2012 | Prada Gomez et al. ........ 382/103 |
| 2002/0169669 | A1 * | 11/2002 | Stetson et al. ................... 705/14 |
| 2006/0048092 | A1 | 3/2006 | Kirkley et al. |
| 2011/0141254 | A1 | 6/2011 | Roebke et al. |
| 2011/0148922 | A1 | 6/2011 | Son et al. |
| 2012/0212499 | A1 | 8/2012 | Haddick et al. |

(Continued)

FOREIGN PATENT DOCUMENTS

AU     2012201615 A1    4/2012

OTHER PUBLICATIONS

Yoshida, et al., "Various Tangible Devices Suitable for Mixed Reality Interactions", Retrieved at <<http://www.rm.is.ritsumei.ac.jp/pdf/yoshida.pdf>>, 9th IEEE International Symposium on Mixed and Augmented Reality (ISMAR), Oct. 13, 2010, pp. 283-284.

(Continued)

*Primary Examiner* — Michelle L Sams
(74) *Attorney, Agent, or Firm* — Heikki Einola; Judy Yee; Micky Minhas

(57) ABSTRACT

A system and related methods for an augmented reality help system in a head-mounted display device are provided. In one example, the head-mounted display device includes a plurality of sensors and a display system for presenting holographic objects. An augmented reality help program is configured to receive one or more user biometric parameters from the plurality of sensors. Based on the user biometric parameters, the program determines that the user is experiencing a stress response, and presents help content to the user via the head-mounted display device.

16 Claims, 6 Drawing Sheets

(56) References Cited

U.S. PATENT DOCUMENTS

| | | | |
|---|---|---|---|
| 2013/0009993 A1* | 1/2013 | Horseman | 345/633 |
| 2013/0044130 A1* | 2/2013 | Geisner et al. | 345/633 |
| 2013/0069985 A1* | 3/2013 | Wong et al. | 345/633 |
| 2013/0083062 A1* | 4/2013 | Geisner et al. | 345/633 |

OTHER PUBLICATIONS

Yusoff, et al., "Users Acceptance on Mixed Reality Technology", Retrieved at <<http://www.iacis.org/iis/2011/194-205_AL2011_1654.pdf>>, Issues in Information Systems vol. XII, (No. 1), Retrieved Date: Apr. 3, 2012, pp. 194-205.

Horan, et al., "MiRTLE: A Mixed Reality Teaching & Learning Environment", Retrieved at <<http://chimera69.essex.ac.uk/@api/deki/files/31/=TR-2009-182.pdf, May 28, 2009, pp. 42.

ISA European Patent Office, International Search Report and Written Opinion for Patent Application No. PCT/US2013/070835, Jan. 21, 2014, 8 pages.

Starner, T. et al., "Augmented Reality Through Wearable Computing", Presence: Teleoperators and Virtual Environments, vol. 6, No. 4, pp. 386-398, Aug. 1997, 24 pages.

* cited by examiner

AUGMENTED REALITY HELP

BACKGROUND

Numerous situations may arise in which a person may benefit from assistance in a variety of contexts. In some examples, assistance may be available in the form of electronic information, which the person may access via an electronic device such as a mobile computing device using a search engine. However, depending upon the current context, locating and accessing such information in a timely and convenient manner may prove challenging and in some cases impractical. Factors that may inhibit such timely and convenient access include the person's location, state of mind, access to an electronic device, current surroundings, and other contextual factors.

Additionally, in some cases and for a variety of possible reasons, a person may experience stress that is related to a situation or current context. For example, a person may have difficulty performing a task and grow frustrated as the number of unsuccessful attempts at completing the task grows. In another example, a person may begin a task or encounter a situation that has proven difficult for other people, yet be unaware of others' similar experiences, or of relevant electronic information that may help the user perform the task. Experiencing stress may also inhibit clear thinking and increase the difficulty of successfully managing a task or situation. Additionally, in some cases and again for a variety of possible reasons, seeking help from electronic devices would impose inconvenient burdens on the person, or may be impractical or even impossible given the person's current context.

SUMMARY

To address the above issues, an augmented reality help system including a head-mounted display device and related methods are provided. In one example, a head-mounted display device is configured to be worn by a user and is operatively connected to a computing device. The head-mounted display device includes a plurality of sensors and a display system for presenting holographic objects. An augmented reality help program may be executed by a processor of the computing device, with the augmented reality help program configured to receive user biometric parameters from one or more of the plurality of sensors. Based on one or more of the user biometric parameters, the augmented reality help program may determine that the user is experiencing a stress response. Based on determining that the user is experiencing the stress response, the augmented reality help program may present help content to the user via the head-mounted display device.

In another example, an augmented reality help system may include a head-mounted display device configured to be worn by a user and operatively connected to a computing device. The head-mounted display device may include a plurality of sensors selected from the group consisting of an optical sensor, a position sensor, an eye-tracking sensor, and a microphone. The head-mounted display device may also include a display system for presenting holographic objects. An augmented reality help program executed by a processor of the computing device may be configured to determine that the user's attention is focused on an object, and may attempt to identify the object. If the augmented reality help program is unable to identify the object, then the program may present default help content to the user. If the augmented reality help program identifies the object, then the program may present to the user either object-specific contextual help content provided by an authorized entity or crowd-sourced object-specific contextual help content that is provided by at least one or more third parties.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Figure 1:
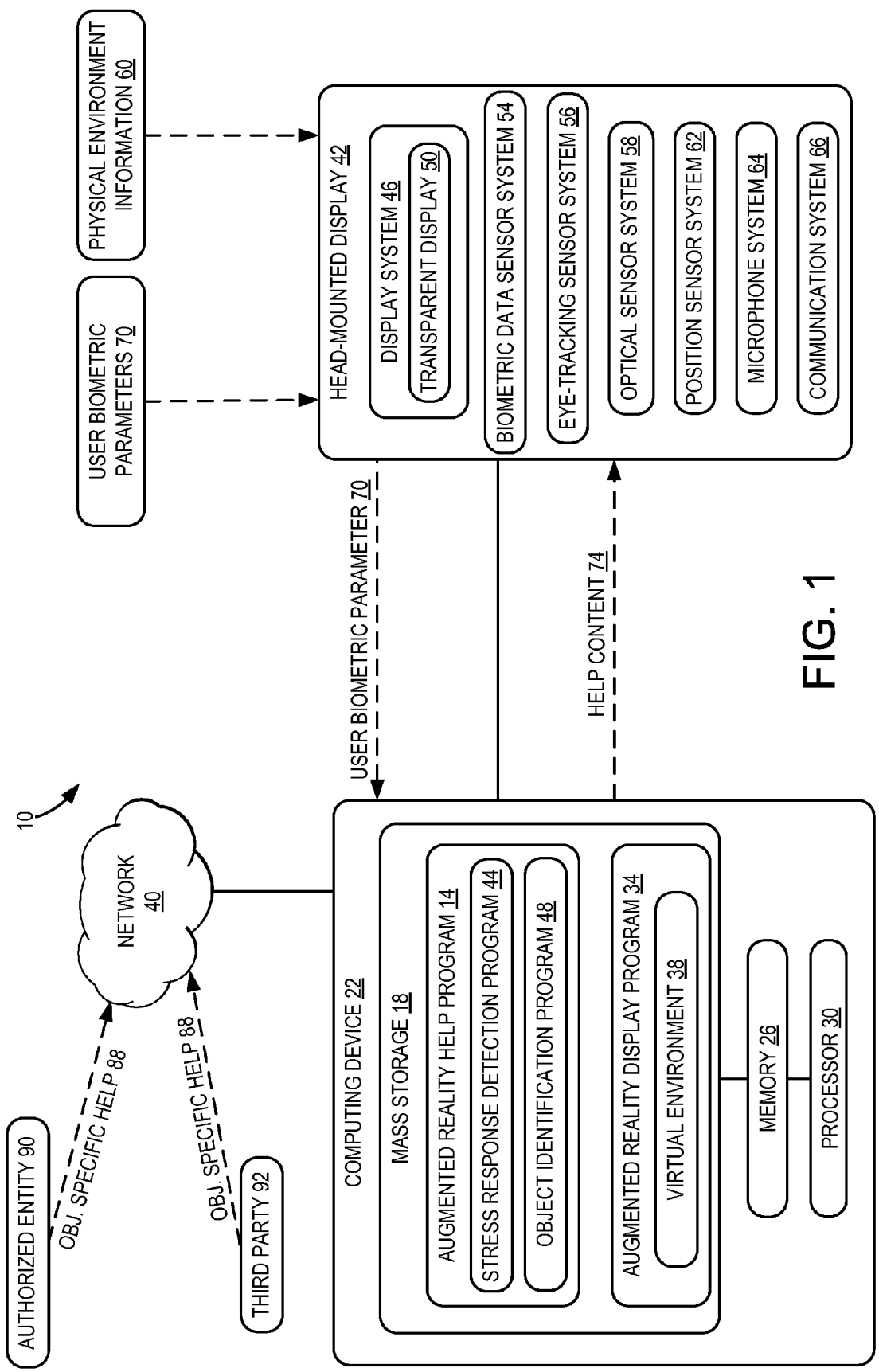
FIG. 1 is a schematic view of an augmented reality help system according to an embodiment of the present disclosure.

FIG. 1 shows a schematic view of one embodiment of an augmented reality help system 10. The augmented reality help system 10 includes an augmented reality help program 14 that may be stored in mass storage 18 of a computing device 22. The augmented reality help program 14 may be loaded into memory 26 and executed by a processor 30 of the computing device 22 to perform one or more of the methods and processes described in more detail below.

In one example, the augmented reality help system 10 may include an augmented reality display program 34 that may be stored in mass storage 18 of the computing device 22. The augmented reality display program 34 may generate a virtual environment 38 for display on a display device, such as the head-mounted display (HMD) device 42. The virtual environment 38 may include one or more virtual object representations, such as holographic objects. In some examples, the virtual environment 38 may be generated to provide an augmented reality experience in the form of an interactive video game, motion picture experience, instructional video, or other suitable experience.

In another example, the augmented reality display program 34 and/or the augmented reality help program 14 may be stored remotely and may be accessed by the computing device 22 over a network to which the computing device is operatively connected, such as network 40.

The computing device 22 may take the form of a desktop computing device, a mobile computing device such as a smart phone, laptop, notebook or tablet computer, network computer, home entertainment computer, interactive television, gaming system, or other suitable type of computing device. Additional details regarding the components and computing aspects of the computing device 22 are described in more detail below with reference to the computing system illustrated in FIG. 8.

The computing device 22 may be operatively connected with the HMD device 42 using a wired connection, or may employ a wireless connection via WiFi, Bluetooth, or any other suitable wireless communication protocol. Additionally, the example illustrated in FIG. 1 shows the computing device 22 as a separate component from the HMD device 42. It will be appreciated that in other examples the computing device 22 may be integrated into the HMD device 42.

The computing device 22 also may be operatively connected with one or more additional devices via network 40. Network 40 may take the form of a local area network (LAN), wide area network (WAN), wired network, wireless network, personal area network, or a combination thereof, and may include the Internet.

Figure 2:
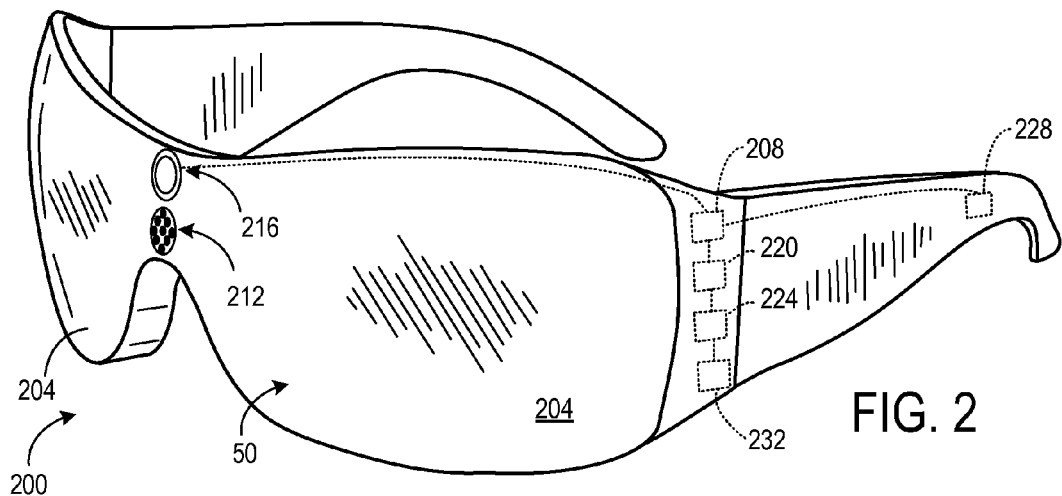
FIG. 2 shows an example head-mounted display device according to an embodiment of the present disclosure.

With reference now also to FIG. 2, one example of an HMD device 200 in the form of a pair of wearable glasses with a transparent display 50 is provided. It will be appreciated that in other examples, the HMD device 200 may take other suitable forms in which a transparent, semi-transparent or non-transparent display is supported in front of a viewer's eye or eyes. It will also be appreciated that the HMD device 42 shown in FIG. 1 may take the form of the HMD device 200, as described in more detail below, or any other suitable HMD device. Additionally, many other types and configurations of display devices having various form factors may also be used within the scope of the present disclosure.

With reference to FIGS. 1 and 2, in this example the HMD device 42 includes a display system 46 and transparent display 50 that enables images to be delivered to the eyes of a user. The transparent display 50 may be configured to visually augment an appearance of a physical environment to a user viewing the physical environment through the transparent display. For example, the appearance of the physical environment may be augmented by graphical content (e.g., one or more pixels each having a respective color and brightness) that is presented via the transparent display 50.

The transparent display 50 may also be configured to enable a user to view a physical, real-world object in the physical environment through one or more partially transparent pixels that are displaying a virtual object representation. In one example, the transparent display 50 may include image-producing elements located within lenses 204 (such as, for example, a see-through Organic Light-Emitting Diode (OLED) display). As another example, the transparent display 50 may include a light modulator on an edge of the lenses 204. In this example, the lenses 204 may serve as a light guide for delivering light from the light modulator to the eyes of a user. Such a light guide may enable a user to perceive a 3D virtual image located within the physical environment that the user is viewing, while also allowing the user to view physical objects in the physical environment.

In other examples, transparent display 50 may support selective filtering of light received from the physical environment before reaching an eye of a user wearing the HMD device 200. Such filtering may be performed on a pixel-by-pixel basis or on groups of pixels. In one example, transparent display 50 may include a first display layer that adds light in the form of one or more illuminated pixels, and a second display layer that filters ambient light received from the physical environment. These layers may have different display resolution, pixel density, and/or display capabilities.

In some examples, the second display layer may include one or more opacity layers in which blocking images may be generated. The one or more opacity layers may be integrally formed within the transparent display 50. In other examples, the one or more opacity layers may be separately mounted or attached adjacent to the transparent display 50, such as in the form of a separate visor.

The HMD device 42 may also include various systems and sensors. For example, the HMD device 42 may include a biometric data sensor system 54 that utilizes one or more sensors 208 to receive and/or detect one or more user biometric parameters 70 from a user of the HMD device. The user biometric parameters 70 may include information related to various physiological processes, functions, measurements, and/or states. Such user biometric parameters 70 may be analyzed by the augmented reality help program 14 to detect a target biologic response, such as a stress response.

In some examples, and as explained in more detail below, one or more user biometric parameters 70 may be utilized by a stress response detection program 44 to determine whether a user is experiencing a stress response. If the user is experiencing a stress response, then the augmented reality help program 14 may be configured to present help content to the user via the HMD device 42.

It will be appreciated that a stress response, also referred to as a fight-or-flight response, may correspond to an arousal of a person's sympathetic nervous system. More particularly, when external and/or internal stimuli trigger a stress response, the hypothalamus may prompt the adrenal glands to release hormones, including adrenaline and cortisol. Among other effects, adrenaline increases the heart rate and elevates blood pressure, while cortisol increases blood sugar and suppresses the immune system.

Emotions and/or experiences that may trigger a stress response include, but are not limited to, situations that elicit frustration, anxiety, excitement, and/or anger. For purposes of this disclosure, a stress response may be defined to include any physiological state that corresponds to an increased level of stress in a person.

The one or more sensors 208 of the biometric data sensor system 54 may include, but are not limited to, a heart rate monitor to measure heart rate, a pulse oximeter sensor to measure hemoglobin saturation, an electrodermal response sensor to monitor the skin's electrical resistance, and an electroencephalographic (EEG) monitor to monitor brainwave activity. The user biometric parameters 70 may include, but are not limited to, heart rate, pupillary response, hemoglobin saturation, skin conductivity, respiration, perspiration, and brainwave activity. As described in more detail below, a user's pupillary response may be detected by an eye-tracking sensor system 56 of the HMD device 42.

The HMD device 42 may include an eye-tracking sensor system 56 that utilizes at least one inward facing sensor 212 (see FIG. 2). The inward facing sensor 212 may be an image sensor that is configured to acquire image data in the form of eye-tracking information from a user's eyes. Provided the user has consented to the acquisition and use of this information, the eye-tracking sensor system 56 may use this information to track a pupillary response, position and/or movement of the user's eyes. The eye-tracking sensor system 56 may then determine where and/or at what physical object or virtual object the user is gazing.

The HMD device 42 may also include an optical sensor system 58 that utilizes at least one outward facing sensor 216, such as an optical sensor. Outward facing sensor 216 may detect movements within its field of view, such as gesture-based inputs or other movements performed by a user or by a person or physical object within the field of view. Outward facing sensor 216 may also capture image information and depth information from a physical environment and physical objects within the environment. For example, outward facing sensor 216 may include a depth camera, a visible light camera, an infrared light camera, and/or a position tracking camera. In some examples, outward facing sensor 216 may include one or more optical sensors for observing visible spectrum and/or infrared light from real-world lighting conditions in the physical environment. Such sensors may include, for example, a charge coupled device image sensor.

As noted above, the HMD device 42 may include depth sensing via one or more depth cameras. Each depth camera may include left and right cameras of a stereoscopic vision system, for example. Time-resolved images from one or more of these depth cameras may be registered to each other and/or to images from another optical sensor such as a visible spectrum camera, and may be combined to yield depth-resolved video.

In some examples, a depth camera may take the form of a structured light depth camera configured to project a structured infrared illumination comprising numerous, discrete features (e.g., lines or points). The depth camera may be configured to image the structured illumination reflected from a scene onto which the structured illumination is projected. A depth map of the scene may be constructed based on spacings between adjacent features in the various regions of an imaged scene.

In other examples, a depth camera may take the form of a time-of-flight depth camera configured to project a pulsed infrared illumination onto a scene. This depth camera may be configured to detect the pulsed illumination reflected from the scene. Two or more of these depth cameras may include electronic shutters synchronized to the pulsed illumination. The integration times for the two or more depth cameras may differ, such that a pixel-resolved time-of-flight of the pulsed illumination, from the source to the scene and then to the depth cameras, is discernable from the relative amounts of light received in corresponding pixels of the two depth cameras. The HMD device 42 may also include an infrared projector to assist in structured light and/or time of flight depth analysis.

In other examples, gesture-based and other motion inputs from the user and/or persons in the physical environment may also be detected via one or more depth cameras. For example, outward facing sensor 216 may include two or more optical sensors with known relative positions for creating depth images. Using motion results from these optical sensors with known relative positions, such depth images may be generated and mapped to gesture-based and other motion inputs.

Outward facing sensor 216 may capture images of a physical environment in which the user is situated. As discussed in more detail below, such images may be part of physical environment information 60 that may be received by the HMD device 42 and provided to the computing device 22. In one example, the augmented reality display program 34 may include a 3D modeling system that uses such input to generate virtual environment 38 that models the physical environment that is captured.

The HMD device 42 may also include a position sensor system 62 that utilizes one or more motion sensors 220 to enable position tracking and/or orientation sensing of the HMD device, and determine a position of the HMD device within a physical environment. For example, the position sensor system 62 may be utilized to determine a head pose orientation of a user's head. In one example, position sensor system 62 may comprise an inertial measurement unit configured as a six-axis or six-degree of freedom position sensor system. This example position sensor system may, for example, include three accelerometers and three gyroscopes to indicate or measure a change in location of the HMD device 42 within three-dimensional space along three orthogonal axes (e.g., x, y, z), and a change in an orientation of the HMD device about the three orthogonal axes (e.g., roll, pitch, yaw).

Position sensor system 62 may support other suitable positioning techniques, such as GPS or other global navigation systems. For example, position sensor system 62 may include a wireless receiver (e.g., a GPS receiver or cellular receiver) to receive wireless signals broadcast from satellites and/or terrestrial base stations. These wireless signals may be used to identify a geographic location of the HMD device 42.

Positioning information obtained from wireless signals received by the HMD device 42 may be combined with positioning information obtained from the motion sensors 220 to provide an indication of location and/or orientation of the HMD device 42. While specific examples of position sensor systems have been described, it will be appreciated that other suitable position sensor systems may be used.

Motion sensors 220 may also be employed as user input devices, such that a user may interact with the HMD device 42 via gestures of the neck and head, or even of the body. Non-limiting examples of motion sensors include an accelerometer, a gyroscope, a compass, and an orientation sensor, which may be included as any combination or subcombination thereof.

The HMD device 42 may also include a microphone system 64 that includes one or more microphones 224. In some examples an array of microphones 224 may receive audio input from a user and/or audio input from a physical environment around the user. Additionally or alternatively, one or more microphones separate from the HMD device 42 may be used to receive audio input.

In other examples, audio may be presented to the user via one or more speakers 228 on the HMD device 42. Such audio may include, for example, music, instructions, and/or other communication from the augmented reality display program 34, the augmented reality help program 14, or other sources.

In other examples, the HMD device 42 may also include a communication system 66 and associated transceiver for broadcasting wireless signals such as Wi-Fi signals, Bluetooth signals, etc., and receiving such signals from other devices. These wireless signals may be used, for example, to exchange data and/or create networks among devices.

The HMD device 42 may also include a processor 232 having a logic subsystem and a storage subsystem, as discussed in more detail below with respect to FIG. 8, that are in communication with the various input and output devices of the HMD device. Briefly, the storage subsystem may include instructions that are executable by the logic subsystem, for example, to receive and forward inputs from the sensors to computing device 22 (in unprocessed or processed form) via the communication system 66, and to present images to the user via the transparent display 50.

It will be appreciated that the HMD device 42 and related sensors and other components described above and illustrated in FIGS. 1 and 2 are provided by way of example. These examples are not intended to be limiting in any manner, as any other suitable sensors, components, and/or combination of sensors and components may be utilized. Therefore it is to be understood that the HMD device 42 may include additional and/or alternative sensors, cameras, microphones, input devices, output devices, etc. without departing from the scope of this disclosure. Further, the physical configuration of the HMD device 42 and its various sensors and subcomponents may take a variety of different forms without departing from the scope of this disclosure.

Figure 3:
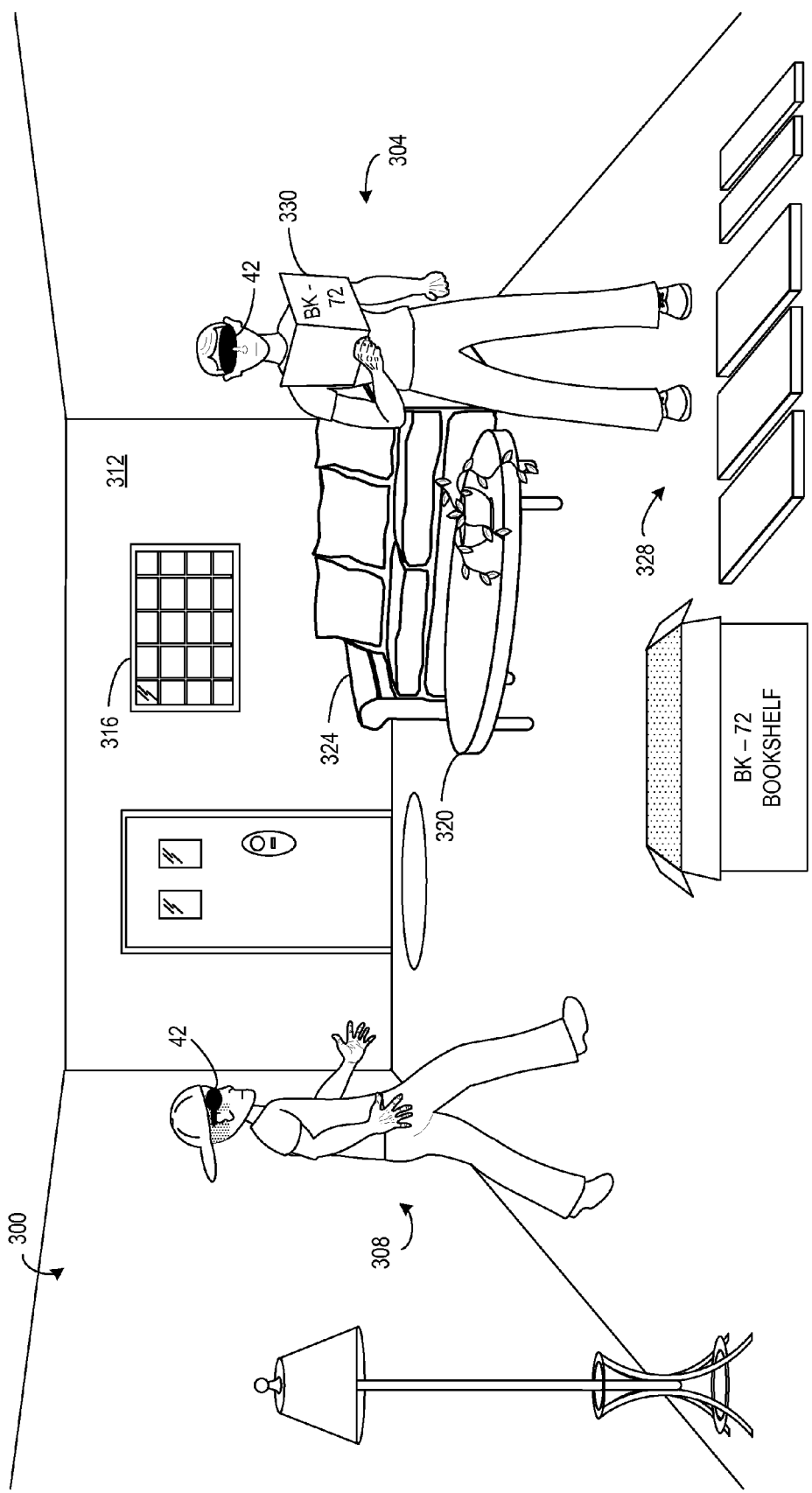
FIG. 3 is a schematic view of two users in a physical environment using the head-mounted display device of FIG. 2 and the augmented reality help system of FIG. 1 according to an embodiment of the present disclosure.

With reference now also to FIG. 3, descriptions of example embodiments and use cases utilizing the augmented reality help system 10 and HMD device 42 will now be provided. FIG. 3 is a schematic illustration of a first user 304 and a second user 308 located in a physical environment. In this example the physical environment is a room 300 that includes physical objects such as a wall 312, a window 316, a coffee table 320 and a couch 324. The first user 304 may wear a first HMD device 42 and the second user 308 may wear a second HMD device 42. The first and second HMD devices 42 may both take the form of HMD device 200.

As described further in the various use cases discussed below, and with reference again to FIG. 1, the augmented reality help program 14 may be configured to receive one or more user biometric parameters 70 from one or more of the plurality of sensors of HMD device 42. Based on one or more of the user biometric parameters 70, the augmented reality help program 14 may determine that a user is experiencing a stress response. Based on determining that the user is experiencing a stress response, the augmented reality help program 14 may present help content 74 to the user via the HMD device 42.

Figure 4:
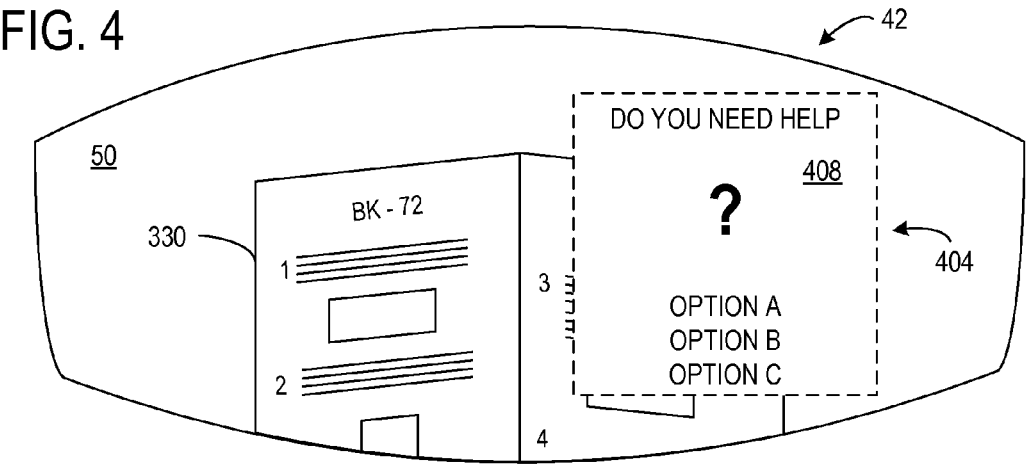
FIG. 4 is a schematic view of a physical environment as seen through the head-mounted display device worn by a first user in FIG. 3 and showing default help content.

In one example and with reference now to FIG. 3, the first user 304 may be attempting to assemble the components of a bookcase 328. The first user 304 may be reading an instruction manual 330 that was provided with the bookcase 328. FIG. 4 shows the first user's view of the instruction manual 330 as seen through the transparent display 50 of the first HMD device 42.

The instructions in instruction manual 330 for assembling the bookcase 328 may be less than clear. The first user 304 may correspondingly experience frustration at the lack of clarity and corresponding difficulty of assembling the bookcase 328. The stress response detection program 44 in the augmented reality help program 14 may receive one or more user biometric parameters 70 that indicate a stress response indicative of such frustration, such as an elevated heartbeat, skin conductivity, and/or brainwave activity that corresponds to a stress response.

Based on determining that the first user 304 is experiencing a stress response, the augmented reality help program 14 may present help content 74 to the user via the first HMD device 42. In one example and with reference again to FIG. 4, the augmented reality help program 14 may present default help content in the form of a general visual query 404 to the first user 304 asking whether the first user needs help. As shown in FIG. 4, in one example the general visual query 404 may comprise a visual help menu 408 that is displayed to the first user 304 via the first HMD device 42. The visual help menu 408 may also include one or more predetermined help options, indicated as Options A, B and C. It will be appreciated that the visual help menu 408 may be displayed in a variety of manners, such as a two-dimensional object, a three-dimensional holographic object, opaque, transparent, etc.

In other examples the general visual query 404 may take a variety of other forms, such as a simple visual icon like a question mark. In still other examples, the default help content may comprise other forms of input or notification to the first user 304, such as an audio query presented via speaker 228 on the first HMD device 42.

In another example, the augmented reality help program 14 may be configured to determine that a user's attention is focused on an object. With reference again to FIG. 3, the augmented reality help program 14 may use data provided by the sensor systems of the HMD device 42 to determine that the first user's attention is focused on the instruction manual 330. For example, the augmented reality help program 14 may use one or more of eye-tracking information, head pose information, and user voice information to determine that the user's attention is focused on the instruction manual 330.

In one example the first user 304 may continuously read the instruction manual 330 for a period of time longer than a threshold period of time, which may indicate that the first user's attention is focused on the manual. Data from the eye-tracking sensor system 56 and the optical sensor system 58 may indicate that the first user 304 is continuously reading the instruction manual 330 for a period longer than the threshold period. Such data may then be used by the augmented reality help program 14 to determine that the first user's attention is focused on the instruction manual 330.

The augmented reality help program 14 may include an object identification program 48 that is configured to attempt to identify the object on which the first user 304 is focused. The object identification program 48 may use data received from the sensor systems of the HMD device 42 to attempt to identify an object. In some examples, the object identification program 48 may ask the first user 304 to identify the instruction manual 330, which may assist the program in searching and identifying the manual. In the present example, if the object identification program 48 is unable to identify the instruction manual 330, then the help content 74 presented to the first user 304 may comprise default help content as described above. If the object identification program 48 identifies the instruction manual 330, then the help content 74 presented to the first user 304 may comprise object-specific contextual help content that is tailored to the object.

Figure 5:
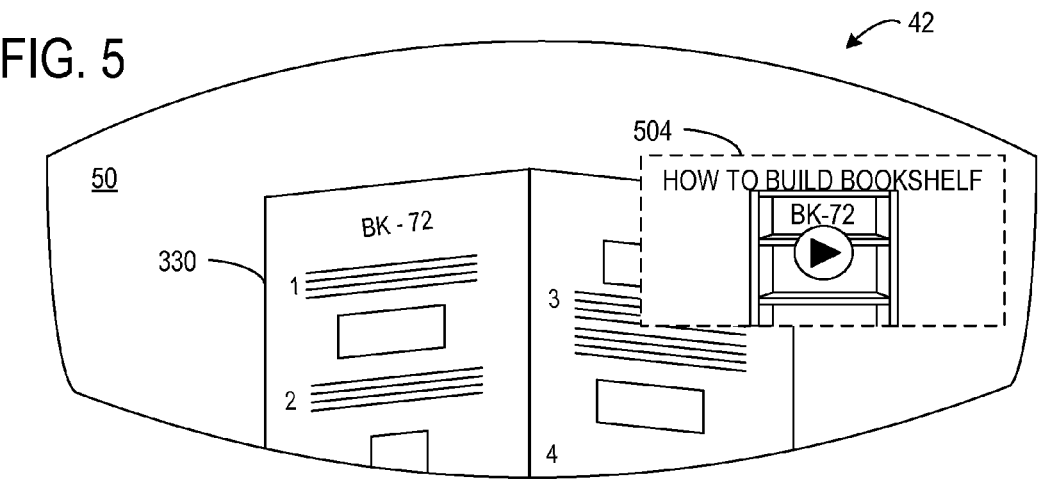
FIG. 5 is a schematic view of a physical environment as seen through the head-mounted display device worn by the first user in FIG. 3 and showing object-specific contextual help content.

With reference now to FIG. 5, in one example the object identification program 48 may identify the instruction manual 330 as the manual for assembling the BK-72 bookcase 328. Upon the augmented reality help program 14 determining that the first user 304 is experiencing a stress response, help content 74 in the form of an instructional video 504 explaining step-by-step how to assemble the BK-72 bookcase 328 may be presented to the first user 304 via the first HMD device 42. In one example, the instructional video 504 may include an augmented reality presentation showing a person assembling the BK-72 bookcase 328.

With reference now to FIG. 1, in one example object-specific contextual help 88 in the form of the instructional video 504 may be provided by an authorized entity 90 and received by the computing device 22 via network 40. In the present example, the authorized entity 90 may comprise a manufacturer, supplier, and/or retailer of the BK-72 bookcase 328. It will be appreciated that an authorized entity 90 may also include any other entity that has a verified association with the BK-72 bookcase.

In another example, object-specific contextual help 88 may comprise crowd-sourced object-specific contextual help content that is provided by one or more third parties 92 and received by the computing device 22 via network 40. The one or more third parties 92 may include individuals, commercial entities, product information services, or any other information sources that have relevant information regarding the BK-72 bookcase 328.

In other examples, at least a portion of the help content 74 may be received by the computing device 22 via other input mechanisms, as described in more detail below with reference to FIG. 8. Further, while the object of the user's attention in this example is a physical object, it will be appreciated that in other examples the augmented reality help program 14 may also determine that the user's attention is focused on a virtual object, such as a holographic object displayed by the HMD device 42. In these examples, the augmented reality help program 14 may present object-specific contextual help content 74 related to the virtual object to the user via the HMD device 42.

In another example, the augmented reality help program 14 may be configured to tailor the object-specific contextual help content to a user based on user-related information. In one use case example and with reference again to FIG. 3, the second user 308 may realize that he is late for a meeting across town. The stress response detection program 44 may receive one or more user biometric parameters 70 of the second user 308 via the second HMD device 42. Based on the user biometric parameters 70, the stress response detection program 44 may determine that the second user 308 is experiencing a stress response.

Figure 6:
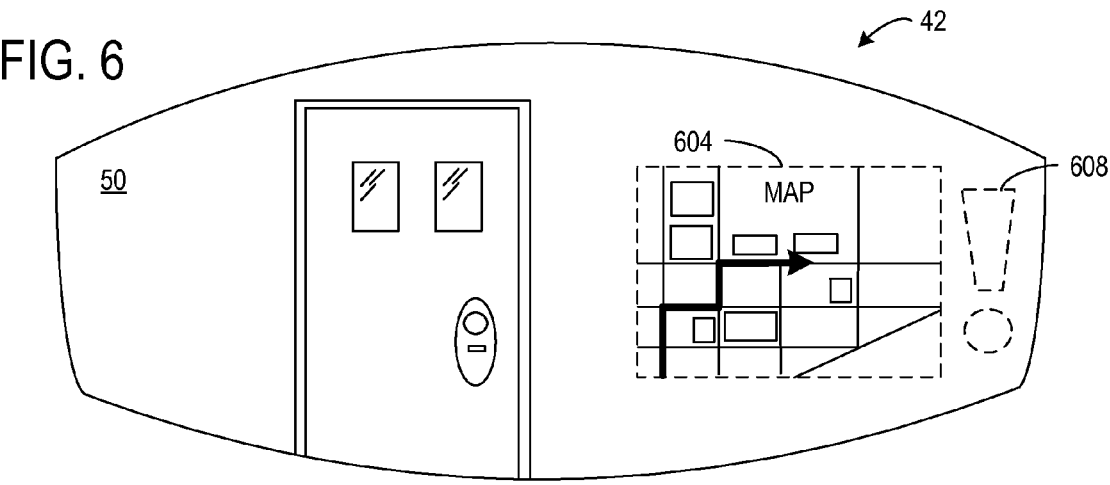
FIG. 6 is a schematic view of a physical environment as seen through the head-mounted display device worn by a second user in FIG. 3 and showing help content.

In one example, the augmented reality help program 14 may further determine from a calendar of the second user 308 that the second user is late for the meeting across town (provided that the second user 308 has consented to allow access to such information). With reference now to FIG. 6 and using the second user's current location, the augmented reality help program 14 may present to the second user 308 a virtual map 604 showing a suggested driving route from the second user's current location to the location of the meeting. The map 604 may further include an alert 608 that communicates a sense of urgency to the second user 308.

User-related information that may be used by the augmented reality help program 14 may include, but is not limited to, location, position, time, calendar, demographic, social graph, and personal preference information. It will be appreciated that any other suitable types and forms of user-related information may be used by the augmented reality help program 14 to tailor object-specific contextual help content to the user. It will also be appreciated that user-related information may not be accessed and/or used by the augmented reality help program 14 without prior consent of the user.

In another user case example, the augmented reality help program 14 may present help content 74 to a user based on determining that a user's attention is focused on an object, and without reference to user biometric parameters. In this example and as described above, the augmented reality help program 14 may use data provided by the sensor systems of the HMD device 42 to determine that the user's attention is focused on a physical or virtual object. If the augmented reality help program 14 is unable to identify the object, then the program may present default help content to the user.

If the augmented reality help program 14 identifies the object, then the program 14 may present to the user either object-specific contextual help content provided by an authorized entity or crowd-sourced object-specific contextual help content that is provided by at least one or more third parties It will also be appreciated that in this example, the HMD device 42 may not include a biometric data sensor system 54.

In another use case example, the augmented reality help program 14 may be further configured to present default help content, object-specific contextual help content, or crowd-sourced object-specific contextual help content to the user based on receiving a request for help from the user. For example, and with reference again to FIG. 3, upon realizing that he is late to the meeting across town, the second user 308 may say, "What is the quickest route to my meeting across town?" The microphone system 64 of the second HMD device 42 may receive this query and relay this data to the augmented reality help program 14. In response, the augmented reality help program 14 may display the virtual map 604 illustrated in FIG. 6 to the second user 308 via the second HMD device 42.

Figure 7A:
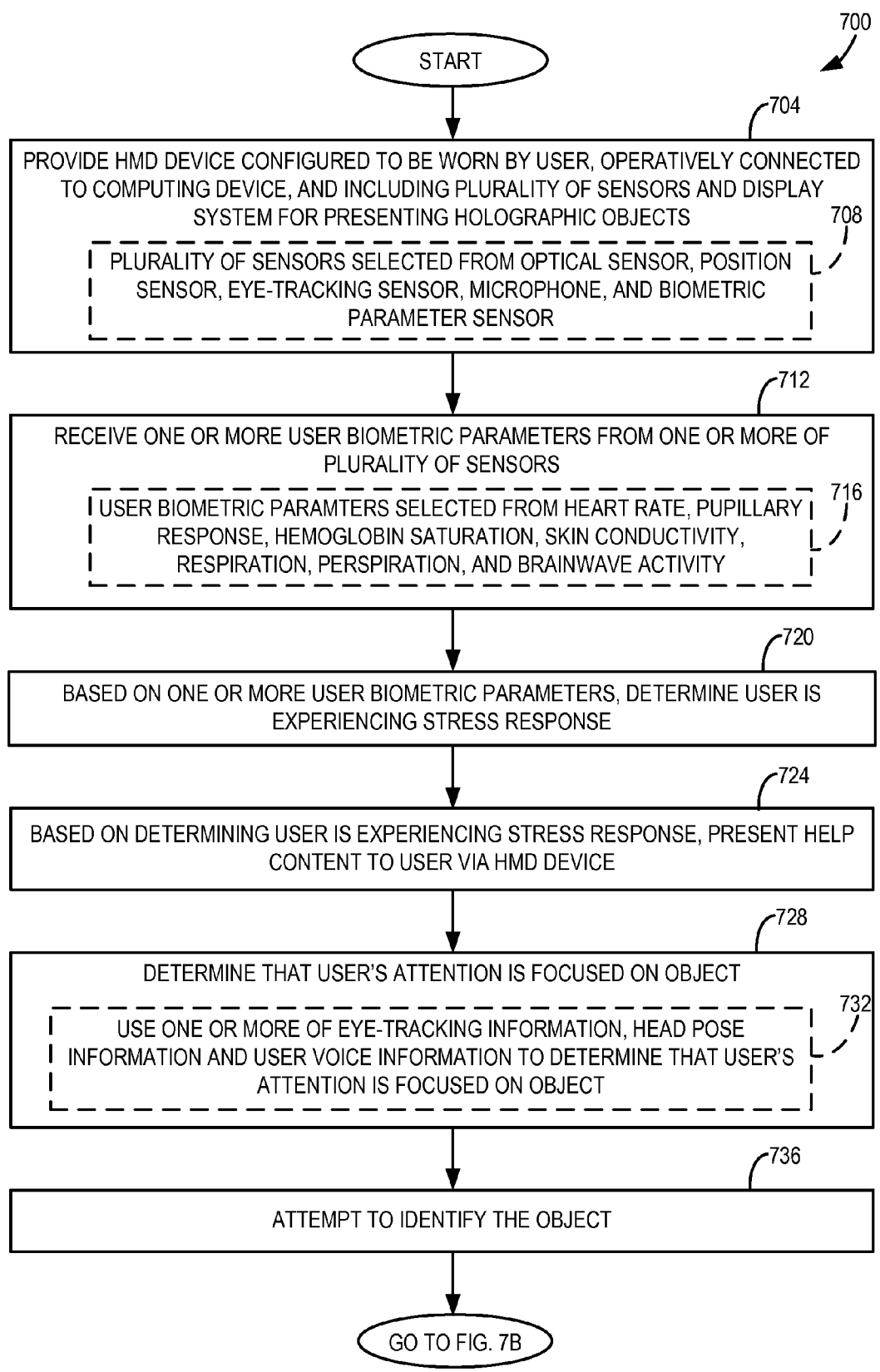
FIGS. 7A and 7B are a flow chart of a method for presenting help content to a user via a head-mounted display device according to an embodiment of the present disclosure.
Figure 7B:
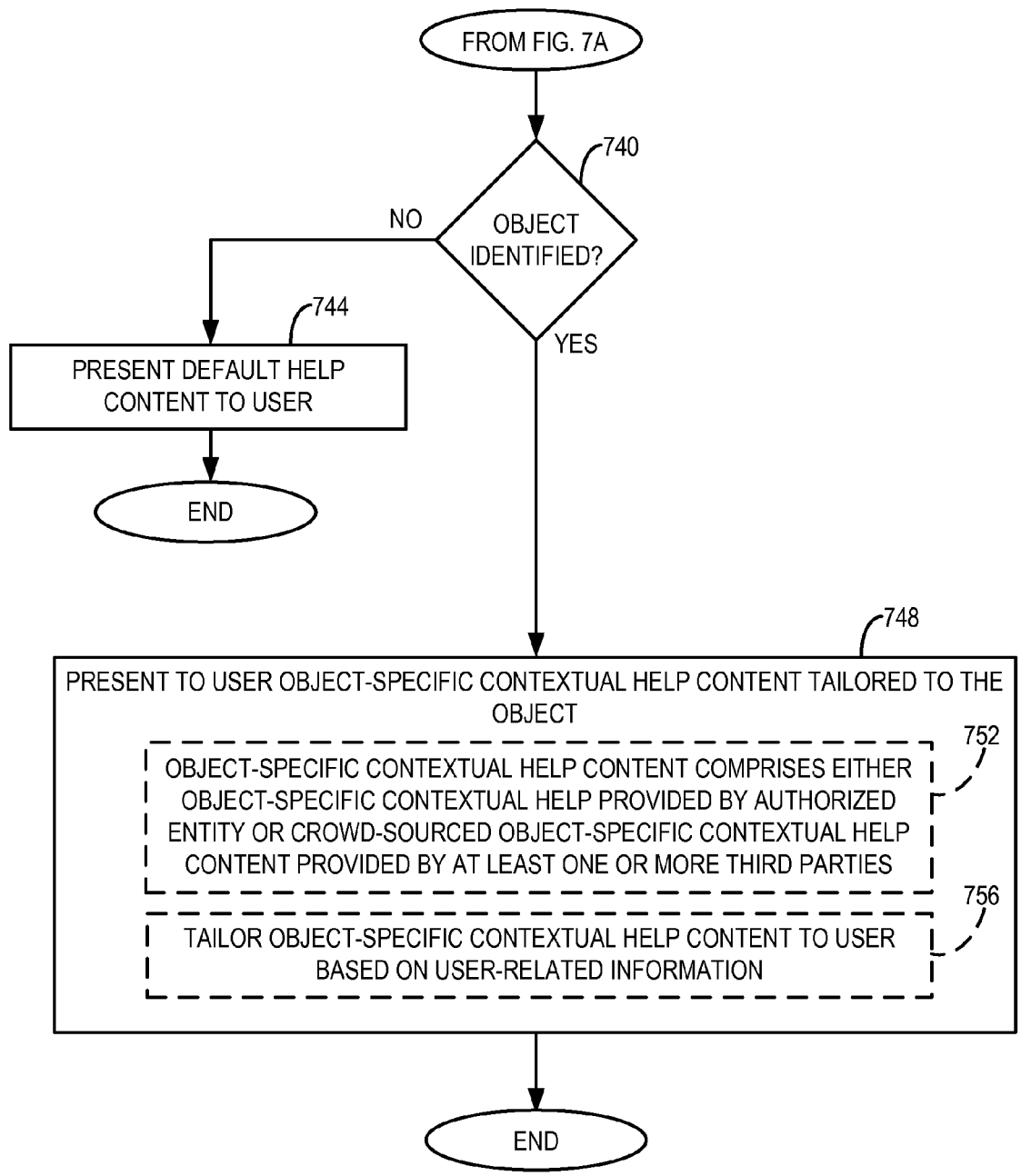

FIGS. 7A and 7B illustrate a flow chart of a method 700 for presenting help content to a user via an HMD device according to an embodiment of the present disclosure. The following description of method 700 is provided with reference to the software and hardware components of the augmented reality help system 10 described above and shown in FIGS. 1-6. It will be appreciated that method 700 may also be performed in other contexts using other suitable hardware and software components.

With reference to FIG. 7A, at 704 the method 700 may include providing an HMD device 42 configured to be worn by a user and operatively connected to a computing device 22, with the HMD device including a plurality of sensors and a display system 46 for presenting holographic objects. At 708 the plurality of sensors may be selected from the group consisting of an optical sensor, a position sensor, an eye-tracking sensor, a microphone, and a biometric parameter sensor.

At 712 the method 700 may include receiving one or more user biometric parameters from one or more of the plurality of sensors. At 716 the one or more user biometric parameters may be selected from the group consisting of heart rate, hemoglobin saturation, skin conductivity, respiration, perspiration, and brainwave activity. At 720 and based on one or more of the user biometric parameters, the method 700 may include determining that the user is experiencing a stress response. At 724 and based on determining that the user is experiencing a stress response, the method 700 may include presenting help content to the user via the HMD device 42.

At 728 the method 700 may further include determining that the user's attention is focused on an object. At 732 the method 700 may include using one or more of eye-tracking information, head pose information, and user voice information to determine that the user's attention is focused on the object. At 736 the method 700 may include attempting to identify the object.

With reference now to FIG. 7B, at 740 the method 700 may attempt to identify the object. If the object is not identified, then at 744 the method 700 may include presenting default help content to the user. After presenting default help content to the user, the method 700 may end. At 748 and where the object is identified, the method 700 may include presenting to the user object-specific contextual help content that is tailored to the object. At 752, the object-specific contextual help content may comprise either object-specific contextual help content provided by an authorized entity or crowd-sourced object-specific contextual help content provided by at least one or more third parties. At 756, the method 700 may further include tailoring the object-specific contextual help content to the user based on user-related information.

Figure 8:
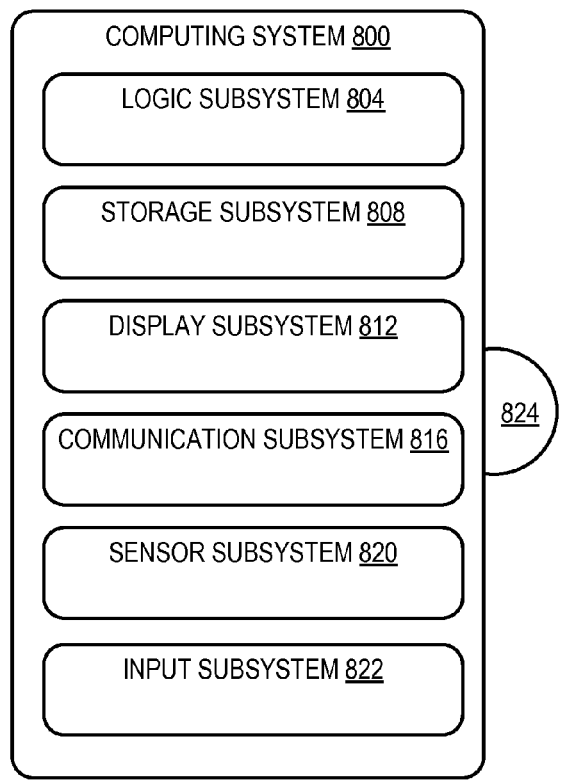
FIG. 8 is a simplified schematic illustration of an embodiment of a computing system.

FIG. 8 schematically shows a nonlimiting embodiment of a computing system 800 that may perform one or more of the above described methods and processes. Computing device 22 may take the form of computing system 800. Computing system 800 is shown in simplified form. It is to be understood that virtually any computer architecture may be used without departing from the scope of this disclosure. In different embodiments, computing system 800 may take the form of a mainframe computer, server computer, desktop computer, laptop computer, tablet computer, home entertainment computer, network computing device, mobile computing device, mobile communication device, gaming device, etc. As noted above, in some examples the computing system 800 may be integrated into an HMD device.

As shown in FIG. 8, computing system 800 includes a logic subsystem 804 and a storage subsystem 808. Computing system 800 may optionally include a display subsystem 812, a communication subsystem 816, a sensor subsystem 820, an input subsystem 822 and/or other subsystems and components not shown in FIG. 8. Computing system 500 may also include computer readable media, with the computer readable media including computer readable storage media and computer readable communication media. Computing system 800 may also optionally include other user input devices such as keyboards, mice, game controllers, and/or touch screens, for example. Further, in some embodiments the methods and processes described herein may be implemented as a computer application, computer service, computer API, computer library, and/or other computer program product in a computing system that includes one or more computers.

Logic subsystem 804 may include one or more physical devices configured to execute one or more instructions. For example, the logic subsystem 804 may be configured to execute one or more instructions that are part of one or more applications, services, programs, routines, libraries, objects, components, data structures, or other logical constructs. Such instructions may be implemented to perform a task, implement a data type, transform the state of one or more devices, or otherwise arrive at a desired result.

The logic subsystem 804 may include one or more processors that are configured to execute software instructions. Additionally or alternatively, the logic subsystem may include one or more hardware or firmware logic machines configured to execute hardware or firmware instructions. Processors of the logic subsystem may be single core or multicore, and the programs executed thereon may be configured for parallel or distributed processing. The logic subsystem may optionally include individual components that are distributed throughout two or more devices, which may be remotely located and/or configured for coordinated processing. One or more aspects of the logic subsystem may be virtualized and executed by remotely accessible networked computing devices configured in a cloud computing configuration.

Storage subsystem 808 may include one or more physical, persistent devices configured to hold data and/or instructions executable by the logic subsystem 804 to implement the herein described methods and processes. When such methods and processes are implemented, the state of storage subsystem 808 may be transformed (e.g., to hold different data).

Storage subsystem 808 may include removable media and/or built-in devices. Storage subsystem 808 may include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Storage subsystem 808 may include devices with one or more of the following characteristics: volatile, nonvolatile, dynamic, static, read/write, read-only, random access, sequential access, location addressable, file addressable, and content addressable.

In some embodiments, aspects of logic subsystem 804 and storage subsystem 808 may be integrated into one or more common devices through which the functionally described herein may be enacted, at least in part. Such hardware-logic components may include field-programmable gate arrays (FPGAs), program- and application-specific integrated circuits (PASIC/ASICs), program- and application-specific standard products (PSSP/ASSPs), system-on-a-chip (SOC) systems, and complex programmable logic devices (CPLDs), for example.

FIG. 8 also shows an aspect of the storage subsystem 808 in the form of removable computer-readable storage media 824, which may be used to store data and/or instructions executable to implement the methods and processes described herein. Removable computer-readable storage media 824 may take the form of CDs, DVDs, HD-DVDs, Blu-Ray Discs, EEPROMs, and/or floppy disks, among others.

It is to be appreciated that storage subsystem 808 includes one or more physical, persistent devices. In contrast, in some embodiments aspects of the instructions described herein may be propagated in a transitory fashion by a pure signal (e.g., an electromagnetic signal, an optical signal, etc.) that is not held by a physical device for at least a finite duration. Furthermore, data and/or other forms of information pertaining to the present disclosure may be propagated by a pure signal via computer-readable communication media.

When included, display subsystem 812 may be used to present a visual representation of data held by storage subsystem 808. As the above described methods and processes change the data held by the storage subsystem 808, and thus transform the state of the storage subsystem, the state of the display subsystem 812 may likewise be transformed to visually represent changes in the underlying data. The display subsystem 812 may include one or more display devices utilizing virtually any type of technology. Such display devices may be combined with logic subsystem 804 and/or storage subsystem 808 in a shared enclosure, or such display devices may be peripheral display devices. The display subsystem 812 may include, for example, the display system 46 and transparent display 50 of the HMD device 42.

When included, communication subsystem 816 may be configured to communicatively couple computing system 800 with one or more networks and/or one or more other computing devices. Communication subsystem 816 may include wired and/or wireless communication devices compatible with one or more different communication protocols. As nonlimiting examples, the communication subsystem 816 may be configured for communication via a wireless telephone network, a wireless local area network, a wired local area network, a wireless wide area network, a wired wide area network, etc. In some embodiments, the communication subsystem may allow computing system 800 to send and/or receive messages to and/or from other devices via a network such as the Internet.

Sensor subsystem 820 may include one or more sensors configured to sense different physical phenomenon (e.g., visible light, infrared light, sound, acceleration, orientation, position, etc.) and/or physiological processes, functions, measurements, and/or states as described above. For example, the sensor subsystem 820 may comprise one or more eye-tracking sensors, image sensors, microphones, motion sensors such as accelerometers, compasses, touch pads, touch screens, heart rate monitors, pulse oximeters, electrodermal response sensors, electroencephalographic (EEG) monitors, and/or any other suitable sensors. Sensor subsystem 820 may be configured to provide observation information to logic subsystem 804, for example. As described above, observation information such as biometric parameter information, eye-tracking information, image information, audio information, ambient lighting information, depth information, position information, motion information, and/or any other suitable sensor data may be used to perform the methods and processes described above.

In some embodiments sensor subsystem 820 may include a depth camera (e.g., outward facing sensor 216 of FIG. 2). The depth camera may include left and right cameras of a stereoscopic vision system, for example. Time-resolved images from both cameras may be registered to each other and combined to yield depth-resolved video. In other embodiments the depth camera may be a structured light depth camera or a time-of-flight camera, as described above In some embodiments, sensor subsystem 820 may include a visible light camera, such as a digital camera. Virtually any type of digital camera technology may be used without departing from the scope of this disclosure. As a non-limiting example, the visible light camera may include a charge coupled device image sensor.

When included, input subsystem 822 may comprise or interface with one or more sensors or user-input devices such as a game controller, gesture input detection device, voice recognizer, inertial measurement unit, keyboard, mouse, or touch screen. In some embodiments, the input subsystem 822 may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

The term "program" may be used to describe an aspect of the augmented reality help system 10 that is implemented to perform one or more particular functions. In some cases, such a program may be instantiated via logic subsystem 804 executing instructions held by storage subsystem 808. It is to be understood that different programs may be instantiated from the same application, service, code block, object, library, routine, API, function, etc. Likewise, the same program may be instantiated by different applications, services, code blocks, objects, routines, APIs, functions, etc. The term "program" is meant to encompass individual or groups of executable files, data files, libraries, drivers, scripts, database records, etc.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated may be performed in the sequence illustrated, in other sequences, in parallel, or in some cases omitted. Likewise, the order of the above-described processes may be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. An augmented reality help system, comprising:
   a head-mounted display device configured to be worn by a user and operatively connected to a computing device, the head-mounted display device including a plurality of sensors and a display system for presenting holographic objects, and
   an augmented reality help program executed by a processor of the computing device, the augmented reality help program configured to:
     receive user biometric parameters from one or more of the plurality of sensors;
     based on one or more of the user biometric parameters, determine that the user is experiencing a stress response;
     determine that the user's attention is focused on an object;
     attempt to identify the object; and
     when the augmented reality help program is unable to identify the object, and based on determining that the user is experiencing the stress response, present default help content to the user via the head-mounted display device.

2. The augmented reality help system of claim 1, wherein the augmented reality help program is further configured to use one or more of eye-tracking information, head pose information, and user voice information to determine that the user's attention is focused on the object.

3. The augmented reality help system of claim 1, wherein when the augmented reality help program identifies the object, the augmented reality help program is further configured to present to the user object-specific contextual help content that is tailored to the object.

4. The augmented reality help system of claim 3, wherein the object-specific contextual help content comprises either object-specific contextual help content provided by an authorized entity or crowd-sourced object-specific contextual help content that is provided by at least one or more third parties.

5. The augmented reality help system of claim 3, wherein the augmented reality help program is further configured to tailor the object-specific contextual help content to the user based on user-related information.

6. The augmented reality help system of claim 1, wherein the plurality of sensors are selected from the group consisting of an optical sensor, a position sensor, an eye-tracking sensor, a microphone, and a biometric parameter sensor.

7. The augmented reality help system of claim 1, wherein the user biometric parameters are selected from the group consisting of heart rate, pupillary response, hemoglobin saturation, skin conductivity, respiration, perspiration, and brainwave activity.

8. A method for presenting help content to a user via a head-mounted display device, comprising:
   providing the head-mounted display device configured to be worn by the user and operatively connected to a computing device, the head-mounted display device including a plurality of sensors and a display system for presenting holographic objects;
   receiving one or more user biometric parameters from one or more of the plurality of sensors;
   based on one or more of the user biometric parameters, determining that the user is experiencing a stress response;
   determining that the user's attention is focused on an object;
   attempting to identify the object; and
   when the augmented reality help program is unable to identify the object, and based on determining that the user is experiencing the stress response, presenting default help content to the user via the head-mounted display device.

9. The method of claim 8, further comprising using one or more of eye-tracking information, head pose information, and user voice information to determine that the user's attention is focused on the object.

10. The method of claim 8, wherein if the object is identified, then presenting to the user object-specific contextual help content that is tailored to the object.

11. The method of claim 10, wherein the object-specific contextual help content comprises either object-specific contextual help content provided by an authorized entity or crowd-sourced object-specific contextual help content that is provided by at least one or more third parties.

12. The method of claim 10, further comprising tailoring the object-specific contextual help content to the user based on user-related information.

13. The method of claim 8, wherein the plurality of sensors are selected from the group consisting of an optical sensor, a position sensor, an eye-tracking sensor, a microphone, and a biometric parameter sensor.

14. The method of claim 8, wherein the user biometric parameters are selected from the group consisting of heart rate, pupillary response, hemoglobin saturation, skin conductivity, respiration, perspiration, and brainwave activity.

15. An augmented reality help system, comprising:
 a head-mounted display device configured to be worn by a user and operatively connected to a computing device, the head-mounted display device including a plurality of sensors selected from the group consisting of an optical sensor, a position sensor, an eye-tracking sensor, and a microphone, the head-mounted display device also including a display system for presenting holographic objects; and
 an augmented reality help program executed by a processor of the computing device, the augmented reality help program configured to:
  determine that the user's attention is focused on an object;
  attempt to identify the object;
  when the augmented reality help program is unable to identify the object, present default help content to the user; and
  when the augmented reality help program identifies the object, present to the user either object-specific contextual help content provided by an authorized entity or crowd-sourced object-specific contextual help content that is provided by at least one or more third parties.

16. The augmented reality help system of claim 15, wherein the augmented reality help program is further configured to present the default help content, the object-specific contextual help content, or the crowd-sourced object-specific contextual help content to the user based on receiving a request for help from the user.

* * * * *